(12) United States Patent
Smith et al.

(10) Patent No.: US 12,055,481 B2
(45) Date of Patent: Aug. 6, 2024

(54) SENSOR DEVICE

(71) Applicant: VIAVI Solutions Inc., San Jose, CA (US)

(72) Inventors: Valton Smith, Novato, CA (US); William D. Houck, Santa Rosa, CA (US); Curtis R. Hruska, Cloverdale, CA (US); Marc K. Von Gunten, Novato, CA (US)

(73) Assignee: VIAVI Solutions Inc., Chandler, AZ (US)

( * ) Notice: Subject to any disclaimer, the term of this patent is extended or adjusted under 35 U.S.C. 154(b) by 0 days.

(21) Appl. No.: 17/447,724

(22) Filed: Sep. 15, 2021

(65) Prior Publication Data

US 2021/0404951 A1 Dec. 30, 2021

Related U.S. Application Data

(63) Continuation of application No. 16/831,308, filed on Mar. 26, 2020, now Pat. No. 11,131,584.
(Continued)

(51) Int. Cl.
  *G01N 21/31* (2006.01)
  *A61B 5/026* (2006.01)
(52) U.S. Cl.
  CPC ............ *G01N 21/31* (2013.01); *A61B 5/0261* (2013.01); *G01N 2201/0633* (2013.01); *G01N 2201/08* (2013.01)
(58) Field of Classification Search
  CPC ........ G01J 3/513; G01J 3/32; G01J 2003/326; G01J 3/0205; G01N 21/31;
(Continued)

(56) References Cited

U.S. PATENT DOCUMENTS 5,148,443 A * 9/1992 Du ..................... H01S 3/08059
  372/99
5,212,099 A * 5/1993 Marcus .............. G01N 21/1717
  422/82.11
(Continued)

FOREIGN PATENT DOCUMENTS

CN 1694644 A 11/2005
CN 107667527 A 2/2018
(Continued)

OTHER PUBLICATIONS

DeMilo C., et al., "Characterization of Penetration Depth As a Function of Optical Fiber Separation At Various Absorption and Scatter Coefficients for a Noninvasive Metabolic Sensor," Proceedings of SPIE, The International Society for Optical Engineering, Jun. 2004, vol. 5317, 11 pages.
(Continued)

*Primary Examiner* — Dominic J Bologna
(74) *Attorney, Agent, or Firm* — Harrity & Harrity, LLP

(57) ABSTRACT

A sensor device may determine a first optical sensor value associated with a first displacement and a second optical sensor value associated with a second displacement, wherein the first displacement is between an emitter associated with the first optical sensor value and a sensing location used to determine the first optical sensor value, wherein the second displacement is between an emitter associated with the second optical sensor value and a sensing location used to determine the second optical sensor value, and wherein the first displacement is different from the second displacement. The sensor device may determine one or more measurements using the first optical sensor value and the second optical sensor value, wherein the one or more measurements relate to a first penetration depth associated with the first
(Continued)

optical sensor value, and a second penetration depth associated with the second optical sensor value.

20 Claims, 9 Drawing Sheets

Related U.S. Application Data

(60) Provisional application No. 62/881,819, filed on Aug. 1, 2019.

(58) Field of Classification Search
CPC ....... G01N 2201/0633; G01N 2201/08; G01N 21/4795; G01N 21/474; A61B 5/0261; A61B 2562/0238; A61B 5/02416; A61B 5/1455; A61B 5/0075
See application file for complete search history.

(56) References Cited

U.S. PATENT DOCUMENTS

| | | | | |
|---|---|---|---|---|
| 5,220,463 A * | 6/1993 | Edelstein | ................. | G02B 5/12 359/857 |
| 5,251,221 A * | 10/1993 | Stultz | ...................... | H01S 3/305 372/101 |
| 5,923,695 A * | 7/1999 | Patel | ........................ | H01S 3/02 372/100 |
| 6,373,866 B1 * | 4/2002 | Black | .................... | H01S 3/0606 372/100 |
| 6,529,276 B1 * | 3/2003 | Myrick | ..................... | G01J 3/42 356/330 |
| 6,769,769 B2 | 8/2004 | Podoleanu et al. | | |
| 7,709,821 B2 * | 5/2010 | Casstevens | ........... | G01J 3/4406 250/573 |
| 9,714,900 B2 * | 7/2017 | Haider | ............... | A61B 5/14539 |
| 10,337,918 B1 * | 7/2019 | Kruspe | ................. | G01J 3/1895 |
| 11,131,584 B2 * | 9/2021 | Smith | ................ | G01N 21/4795 |
| 11,209,265 B2 | 12/2021 | Konolige | | |
| 2002/0080367 A1 * | 6/2002 | Asami | ........................ | G01J 3/10 356/519 |
| 2003/0220549 A1 * | 11/2003 | Liu | ....................... | A61B 5/0059 600/317 |
| 2003/0227628 A1 * | 12/2003 | Kreimer | ................ | G01J 3/0205 356/419 |
| 2006/0181710 A1 * | 8/2006 | Kachanov | .............. | G01N 21/39 356/437 |
| 2007/0097378 A1 * | 5/2007 | Kauppinen | ............ | G01J 3/4535 356/450 |
| 2008/0021330 A1 * | 1/2008 | Hwang | ................. | A61B 5/0059 600/476 |
| 2008/0312533 A1 * | 12/2008 | Balberg | ............... | A61B 8/4227 600/437 |
| 2009/0109442 A1 * | 4/2009 | Felix | ..................... | G01J 3/4535 359/485.06 |
| 2010/0065726 A1 * | 3/2010 | Zhong | ................ | G01N 21/6454 250/227.24 |
| 2011/0075687 A1 * | 3/2011 | Gokay | ................ | H01S 3/09415 372/66 |
| 2012/0012691 A1 * | 1/2012 | Dryer | ....................... | F41G 7/226 244/3.16 |
| 2012/0103099 A1 * | 5/2012 | Stuke | ..................... | B82Y 30/00 977/956 |
| 2014/0275869 A1 * | 9/2014 | Kintz | .................... | A61B 5/1459 600/310 |
| 2015/0109617 A1 * | 4/2015 | Gilbert | ................. | A61B 5/0075 250/234 |
| 2015/0226665 A1 * | 8/2015 | Weidmann | ................. | G01J 3/42 356/437 |
| 2016/0138958 A1 * | 5/2016 | Truong | .................. | G01F 23/292 250/227.28 |
| 2016/0151002 A1 * | 6/2016 | Ruchti | ................ | A61B 5/14532 600/310 |
| 2017/0176336 A1 * | 6/2017 | Dimitriadis | ............ | A61B 1/043 |
| 2017/0244218 A1 * | 8/2017 | Oh | .......................... | H01S 5/0028 |
| 2018/0024040 A1 * | 1/2018 | Yan | ........................ | G01J 3/0256 435/288.7 |
| 2018/0238791 A1 * | 8/2018 | Limodehi | ............ | G01N 21/553 |
| 2019/0128734 A1 * | 5/2019 | Arbore | ....................... | G01J 3/36 |
| 2019/0150763 A1 * | 5/2019 | Gladshtein | ......... | A61B 5/02007 |
| 2019/0277695 A1 * | 9/2019 | Gensemer | ................. | G01J 3/42 |
| 2020/0029870 A1 * | 1/2020 | Jung | .................... | A61B 5/4519 |
| 2020/0196918 A1 * | 6/2020 | Itzkovich | ............. | A61B 5/7221 |
| 2020/0300704 A1 * | 9/2020 | Sekine | ...................... | G01J 3/44 |
| 2020/0315473 A1 * | 10/2020 | Peterson | ............ | A61B 5/02416 |
| 2021/0100485 A1 * | 4/2021 | Nam | .................... | A61B 5/0059 |
| 2021/0262980 A1 * | 8/2021 | Takahashi | ........ | G01N 27/44756 |
| 2022/0020617 A1 * | 1/2022 | Chakarian | .......... | G01N 33/0009 |

FOREIGN PATENT DOCUMENTS

| | | |
|---|---|---|
| EP | 1922989 A2 | 5/2008 |
| KR | 20070048877 A | 5/2007 |

OTHER PUBLICATIONS

Extended European Search Report for Application No. EP20188765.0, mailed on Dec. 10, 2020, 9 pages.

"Sixty Hydration Monitor," 8 pages, [retrieved on Mar. 26, 2020] Retrieved from the internet [URL: https://sixty.ie].

Medgadget, "Reflectance Medical CareGuide Oximeter for Muscle Oxygen Saturation Cleared in U.S.", Aug. 2, 2012, 3 pages, [Retrieved on Mar. 26, 2020] Retrieved from the internet [URL: https://www.medgadgel.com/2012/08/reflectance-medical-careguide-oximeter-for-muscle-oxygen-saturation-cleared-in-u-s.html].

* cited by examiner

SENSOR DEVICE

RELATED APPLICATION(S)

This application is a continuation of U.S. patent application Ser. No. 16/831,308, filed Mar. 26, 2020 (now U.S. Pat. No. 11,131,584), entitled "SENSOR DEVICE," which claims priority to U.S. Provisional Patent Application No. 62/881,819, filed on Aug. 1, 2019, entitled "OPTICAL SENSOR," the contents of which are incorporated herein by reference in their entireties.

BACKGROUND

A sensor device may be utilized to capture information for spectrometry analysis. For example, the sensor device may capture information relating to a set of electromagnetic frequencies. The sensor device may include a set of sensor elements (e.g., optical sensors, spectral sensors, and/or image sensors) that capture the information. For example, an array of sensor elements may be utilized to capture information relating to one or more frequencies. An analysis may be performed on the information relating to the one or more frequencies to determine spectrometry information.

SUMMARY

According to some implementations, a method may include determining a first optical sensor value associated with a first displacement and a second optical sensor value associated with a second displacement, wherein the first displacement is different from the second displacement; determining one or more measurements using the first optical sensor value and the second optical sensor value, wherein the one or more measurements relate to a first penetration depth associated with the first optical sensor value, and a second penetration depth associated with the second optical sensor value; and providing information identifying the one or more measurements.

According to some implementations, a sensor may include one or more optical sensors, and one or more processors configured to determine a first optical sensor value and a second optical sensor value using the one or more optical sensors, wherein the first displacement is different from the second displacement; determine one or more measurements using the first optical sensor value and the second optical sensor value, wherein the one or more measurements relate to a first penetration depth associated with the first optical sensor value, and a second penetration depth associated with the second optical sensor value; and provide information identifying the one or more measurements.

According to some implementations, a device may include one or more optical sensors, and one or more processors, communicatively coupled to the one or more optical sensors, configured to determine a first optical sensor value and a second optical sensor value using the one or more optical sensors, wherein the first displacement is different from the second displacement; determine one or more measurements using the first optical sensor value and the second optical sensor value, wherein the one or more measurements relate to a first penetration depth associated with the first optical sensor value, and a second penetration depth associated with the second optical sensor value; and provide information identifying the one or more measurements.

DETAILED DESCRIPTION

Figure 1:
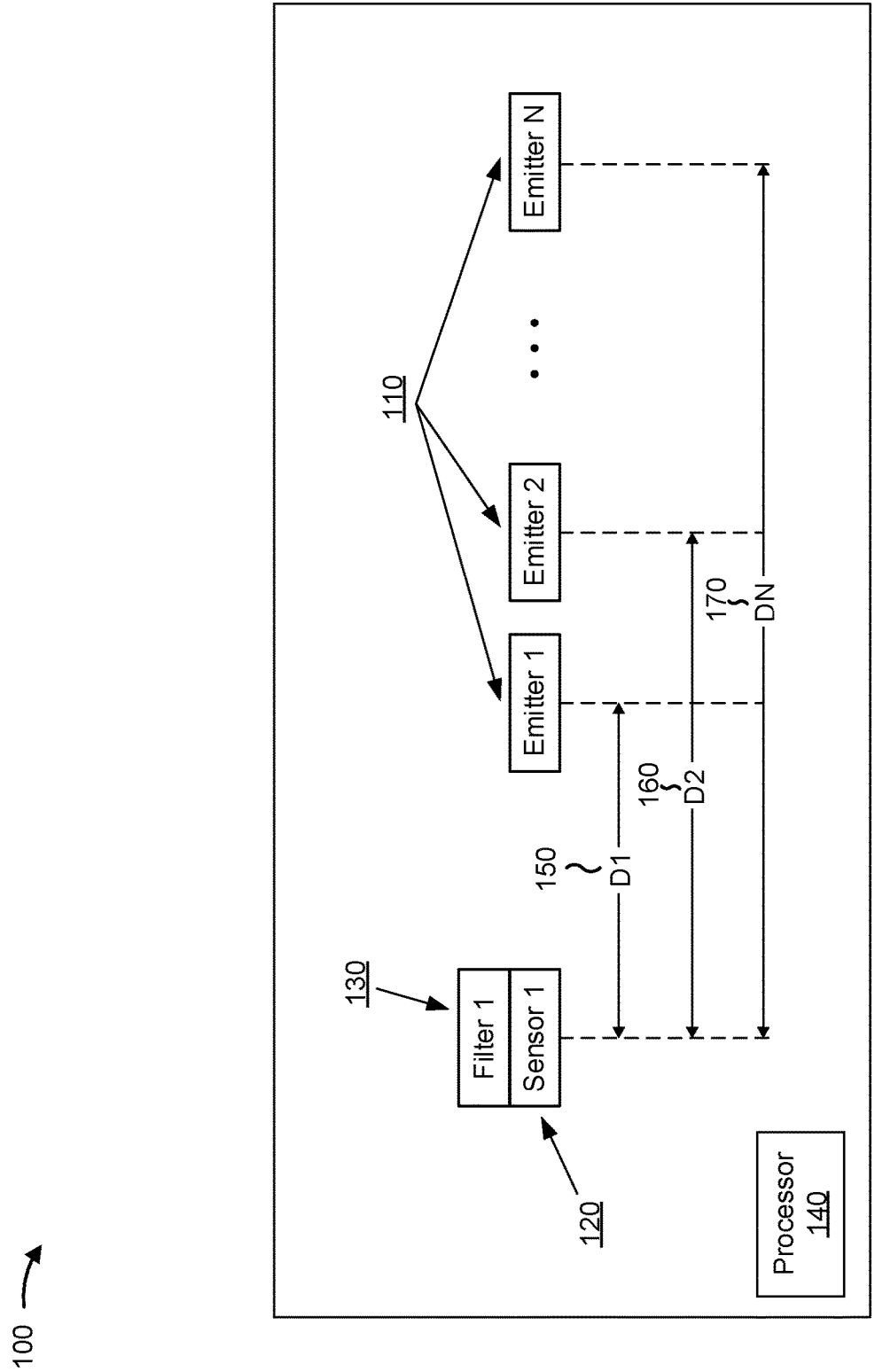
FIGS. 1-5 are diagrams of one or more example implementations described herein.

The following detailed description of example implementations refers to the accompanying drawings. The same reference numbers in different drawings may identify the same or similar elements. The following description uses a spectrometer as an example. However, the calibration principles, procedures, and methods described herein may be used with any sensor, including but not limited to other optical sensors and spectral sensors.

A structure of a measurement target may be composed of layers of different thicknesses. Examples of measurement targets include animal tissue, human tissue, a food item, an organic material, and/or the like. In the case of tissue, different tissue layers contain different types of blood vessels, such as arteries, arterioles, capillaries, and veins. When performing non-intrusive optical measurements of vital signs, blood flow through these different vessels indicates different information. For example, optically monitoring blood pressure is more accurate when measuring blood flow from the deep arteries that exist in the subcutaneous tissue. Measurement complications arise when acquiring spectra of blood flow through deeper layers of tissue (e.g., subcutaneous tissue) because the signal becomes convoluted with signals from the shallower layers (e.g., the dermis and/or epidermis).

A multi-distant approach, in which both deep and shallow layers are assessed, can produce more accurate measurements of blood flow in the deeper vessels, resulting in significantly more accurate readings relative to a single-distant approach. More generally, it may be beneficial to perform measurements at multiple different depths in a measurement sample to determine different types of measurement values or a particular measurement value at two or more different depths. This may be useful, for example, for spectral measurement of a measurement target based on interactance spectrometry. When performing spectral measurements of tissue in interactance mode, the penetration depth of the measured light may be based on a separation between an emitter and a sensor. For example, as the separation increases, the sensor may measure light that has penetrated to a greater penetration depth in the measurement target. However, achieving multiple, different penetration depths using multiple different sensor devices associated with respective sensor/emitter displacements may be costly and size-prohibitive.

Implementations described herein provide interactance-based measurements at multiple different penetration depths in a measurement target. For example, a sensor device may include one or more sensors and one or more emitters. In some implementations, the sensor device may include a single sensor and two or more emitters at different displacements from the single sensor. In some implementations, the sensor device may include a single emitter and two or more sensors at different displacements from the single emitter. In some implementations, the sensor device may include two or more sensors and two or more emitters, which enables measurements at four or more possible displacements between sensor/emitter pairs. In some implementations, the sensor device may include one or more waveguides that guide light from different measurement locations on a measurement target to one or more sensors, thereby achieving different displacements from a single emitter for a single sensor. Thus, the spectra of multiple measurement depths can be measured by including multiple distances between one or more emitters and one or more sensors of a single sensor device, which may provide a lower cost, lower resource consumption, and smaller size than using multiple sensor devices that are each associated with a respective sensor/emitter displacement.

FIGS. 1-5 are diagrams of example implementations of sensor devices 100, 200, 300, 400, and 500 described herein.

FIG. 1 shows an example implementation of a sensor device 100 that includes multiple emitters 110 and a single sensor 120. As shown, sensor device 100 includes multiple emitters 110 (e.g., emitters 1 through N, where N is greater than 1), a single sensor 120, a filter 130 corresponding to the sensor 120, and a processor 140.

Emitter 110 includes an optical transmitter (e.g., a light source) that transmits an optical signal toward a measurement target (not shown). The optical signal may comprise multiple wavelength ranges of visible light, near-infrared light, mid-infrared light, and/or the like. In some implementations, emitter 110 may include a light emitting diode (LED) or an array of LEDs.

Sensor 120 includes a device capable of performing a measurement of light directed toward sensor 120 (e.g., via filter 130), such as an optical sensor, a spectral sensor, an image sensor, and/or the like. Sensor 120 may utilize one or more sensor technologies, such as a complementary metal-oxide-semiconductor (CMOS) technology, a charge-coupled device (CCD) technology, and/or the like. In some implementations, sensor 120 may include multiple sensor elements (e.g., an array of sensor elements—referred to as a sensor array) each configured to obtain information. For example, a sensor element may provide an indication of intensity of light that is incident on the sensor element (e.g., active/inactive or a more granular indication of intensity), such as an electrical signal.

Filter 130 includes a spectral filter, a multispectral filter, a bandpass filter, a blocking filter, a long-wave pass filter, a short-wave pass filter, a dichroic filter, a linear variable filter (LVF), a circular variable filter (CVF), a Fabry-Perot filter, a Bayer filter, and/or the like. Filter 130 may pass one or more wavelengths of light for sensing by sensor 120. In some implementations, filter 130 may include multiple, different filters that are configured to pass respective spectral ranges to sensor 120. For example, filter 130 may include a binary filter, such as a binary multispectral filter.

Processor 140 is described in more detail in connection with FIG. 8.

Emitters 110 of sensor device 100 may be spatially separated from each other so as to achieve different displacements 150, 160, and 170 relative to sensor 120. For example, Emitter 1 is associated with a displacement D1, Emitter 2 is associated with a displacement D2, and so on, where each of these displacements is different than the other displacements. The different displacements D1 through DN may enable measurement at different penetration depths by sensor 120. In some aspects, the displacements D1 through DN may be based on a penetration depth and/or a material composition of the material being measured. For example, a displacement of approximately 1 mm may be used for a shallow skin layer measurement, whereas a displacement of approximately 200 mm may be used for a deep muscle measurement.

In some implementations, an emitter 110 associated with a larger displacement from sensor 120 may emit more optical power than an emitter 110 associated with a smaller displacement from sensor 120. For example, Emitter 2 may use a higher transmission power than Emitter 1. This may improve measurement signal-to-noise ratio and enable the determination of measurements at deeper penetration depths than if each emitter 110 used the same transmission power.

Sensor device 100 may employ a variety of techniques, or a combination of techniques, to differentiate the light transmitted by the emitters 110 and/or the measurements determined using the light. For example, sensor device 100 may activate emitters 110 at different times or in a particular pattern, and may determine measurements for emitters 110 based on the times or the particular pattern. As another example, emitters 110 may emit light at different wavelengths, and filter 130 may filter the different wavelengths so that wavelengths corresponding to different emitters 110 are detected by different regions of sensor 120 or at different times.

Figure 2:
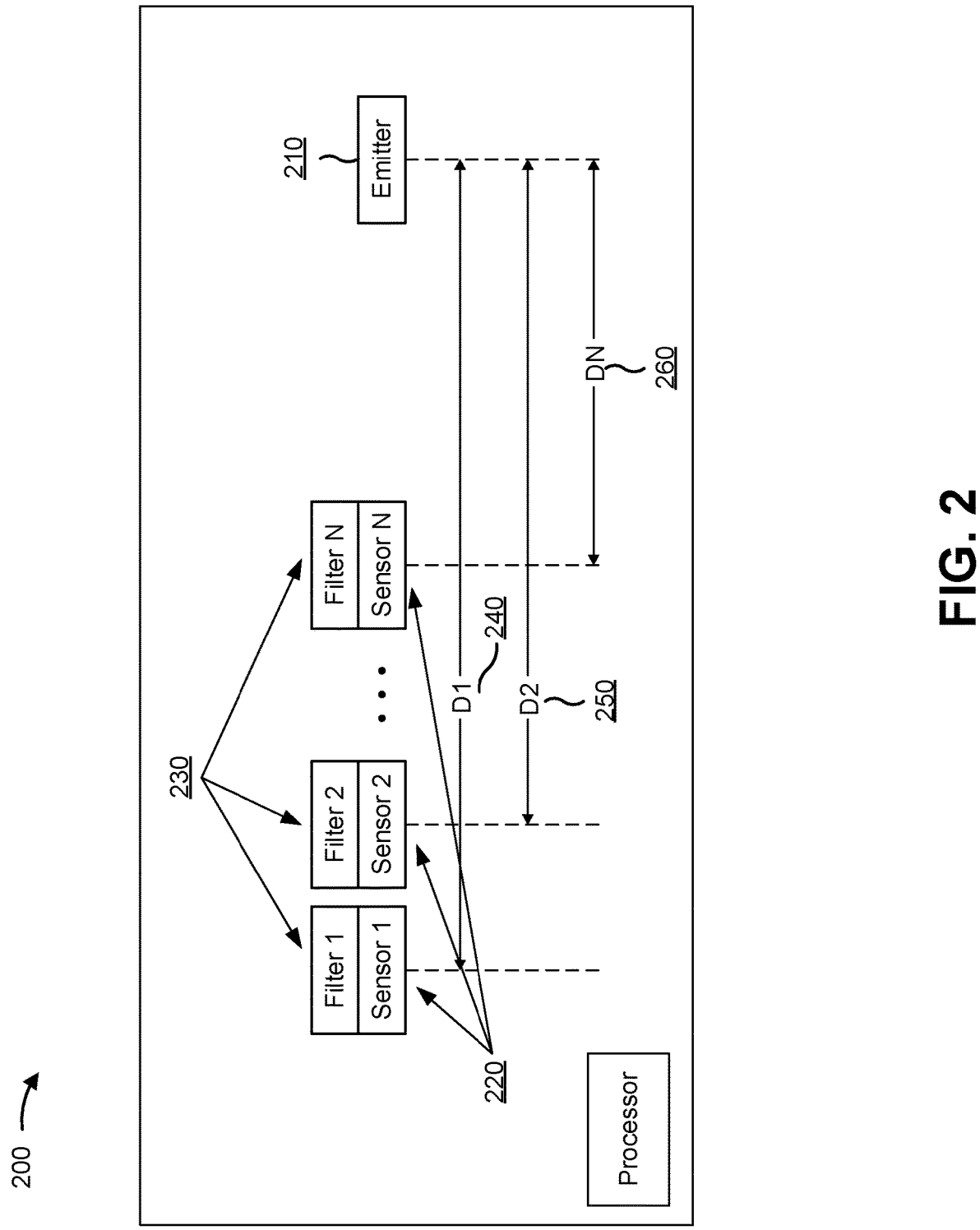

FIG. 2 shows an example implementation of a sensor device 200 that includes a single emitter 210 and multiple sensors 220. As shown, sensor device 200 includes an emitter 210 (e.g., emitter 110), a plurality of sensors 220 (e.g., Sensors 1 through N) (e.g., sensor 120), a plurality of filters 230 (e.g., filter 130) corresponding to the plurality of sensors 220, and a processor (e.g., processor 140). It should be noted that some implementations described herein may not include filters 230, or the filtering function may be integrated with the sensor or performed by another component of sensor device 200 or another sensor device described herein.

As further shown, the plurality of sensors 220 are spaced from emitter 210 at different displacements D1 through DN (shown by reference numbers 240, 250, and 260). For example, D1 through DN may be different from each other, thereby enabling multi-distant spectral measurement of a measurement target. In this case, a sensor 220 farther from emitter 210 (e.g., with a larger displacement) may use a longer integration time for a measurement than a sensor 220 closer to emitter 210 (e.g., with a smaller displacement), which may improve a signal-to-noise ratio for the sensor 220 farther from emitter 210 due to the dimmer signal associated with the larger displacement.

Figure 3:
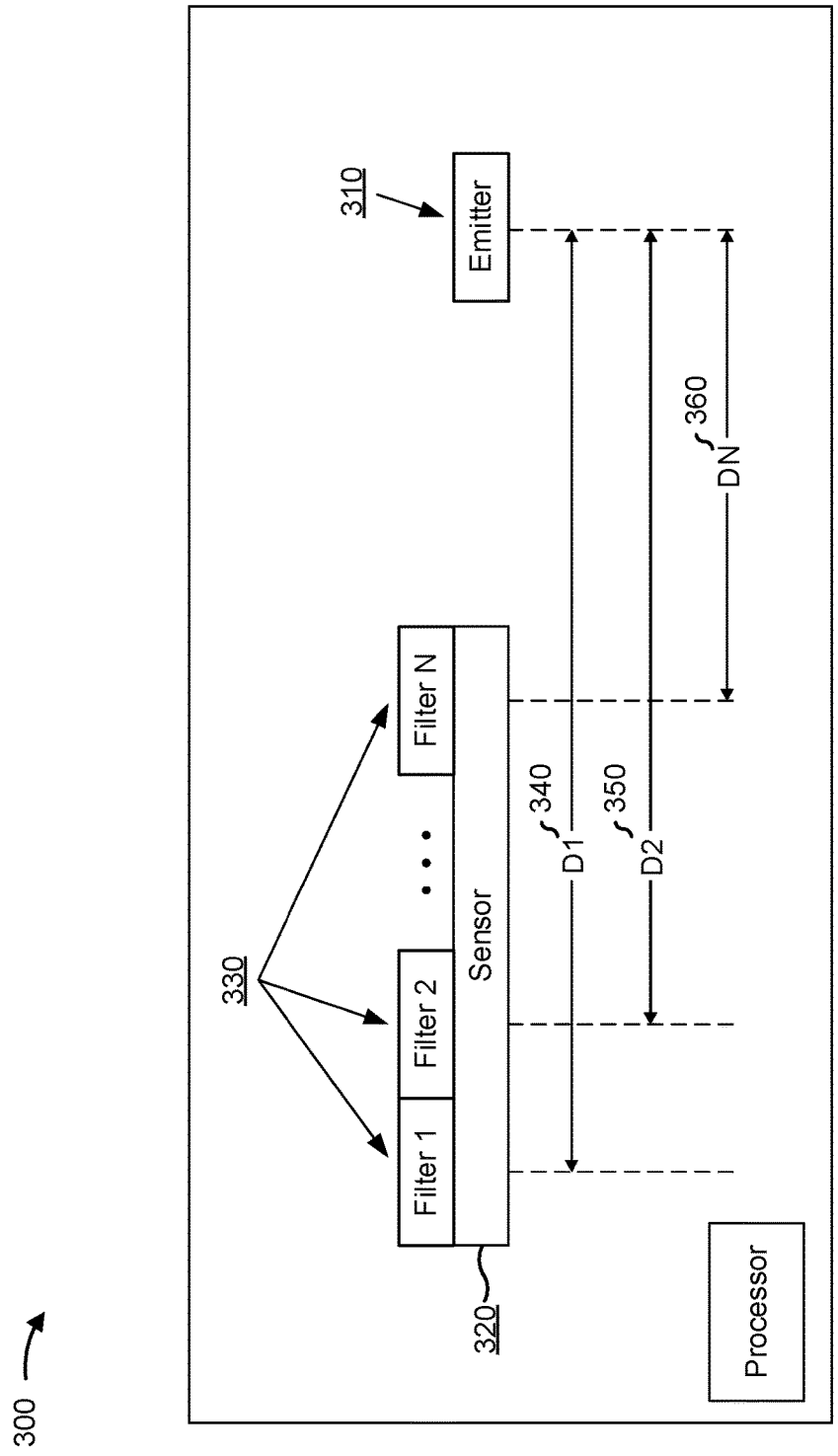

FIG. 3 shows an example implementation 300 that includes a single emitter 310 and a single sensor 320 with multiple sensing locations corresponding to respective filters 330. As shown, sensor device 300 includes an emitter 310 (e.g., emitter 110/210), a sensor 320 (e.g., sensor 120/220), a plurality of filters 330 (e.g., filter 130/320), and a processor (e.g., processor 140). For example, sensor 320 may be associated with a plurality of filters 330 (filters 1 through N). Each filter 330 may be associated with a respective displacement D1 through DN (shown by reference numbers 340, 350, and 360). In some aspects, each filter 330 may cover or be associated with a respective sensing location of sensor 320.

In some aspects, sensor 320 may include a single sensor. For example, sensor 320 may be monolithic and/or may be associated with a single processor, a single backend, a single chip, and/or the like. This may be less costly than implementing a plurality of sensors. In some aspects, sensor 320 may be a composite of multiple sensors, such as a plurality of sensors that are combined to form a sensor, which may be less complex than implementing a single, larger sensor. Each filter 330 may be associated with a respective sensing location. A sensing location may correspond to a range of pixels, an optical detector or set of optical detectors, and/or the like.

Figure 4:
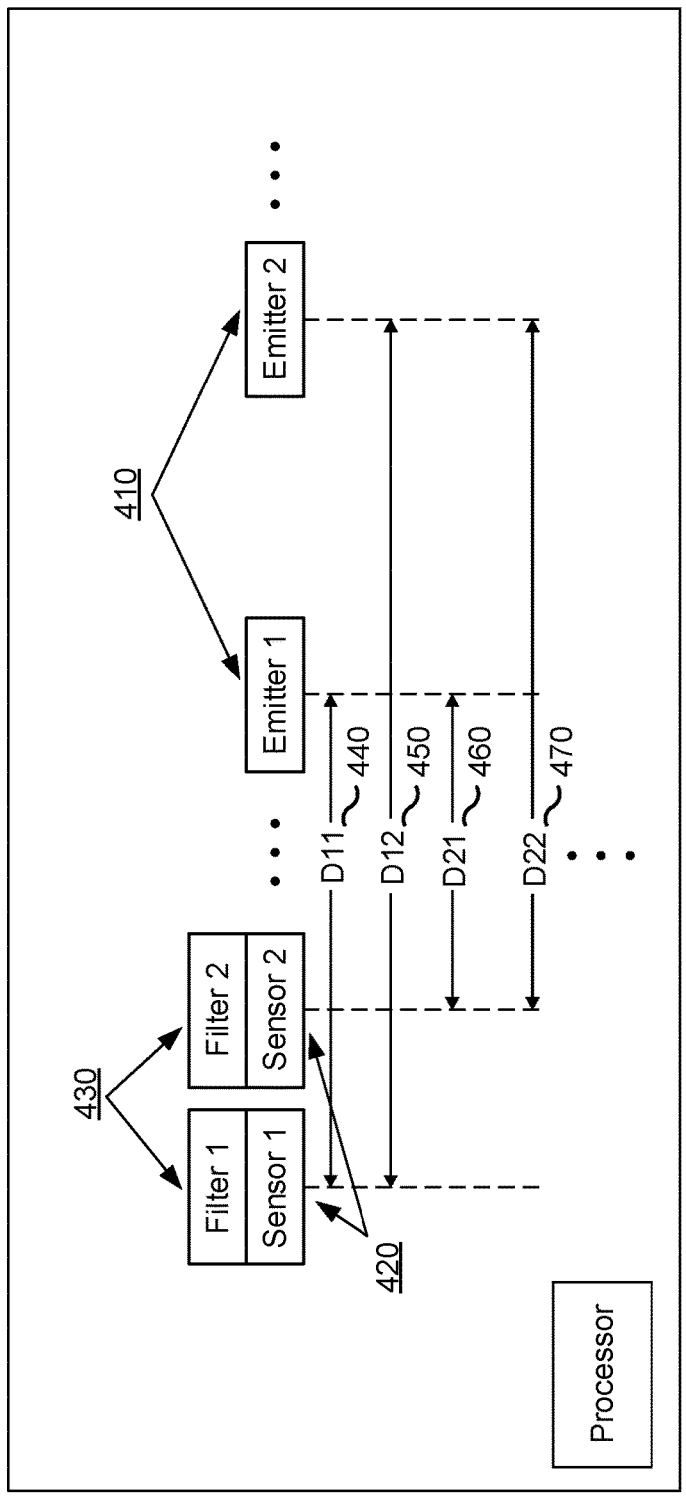

FIG. 4 shows an example implementation of a sensor device 400 that includes multiple emitters 410 and multiple sensors 420. As shown, sensor device 400 includes a plurality of emitters 410 (e.g., emitter 110/210/310), a plurality of sensors 420 (e.g., sensor 120/220/320), a plurality of filters 430 (e.g., filter 130/230/330) corresponding to the plurality of sensors 420, and a processor (e.g., processor 140). As further shown, the plurality of sensors 420 are spaced from the plurality of emitters 410 by respective displacements D11, D12, D21, and D22 (shown by reference numbers 440, 450, 460, and 470, respectively). D11 is a distance from Sensor 1 to Emitter 1, D12 is a distance from Sensor 1 to Emitter 2, D21 is a distance from Sensor 2 to Emitter 1, and D22 is a distance from Sensor 2 to Emitter 2. In some aspects, D11, D12, D21, and D22 may all be different from one another. In some aspects, at least two of D11, D12, D21, and D22 may be equal to one another. By implementing multiple sensors and multiple emitters, the number of displacements between sensors and emitters can be up to S×E, where S is a number of sensors and E is a number of emitters.

Figure 5:
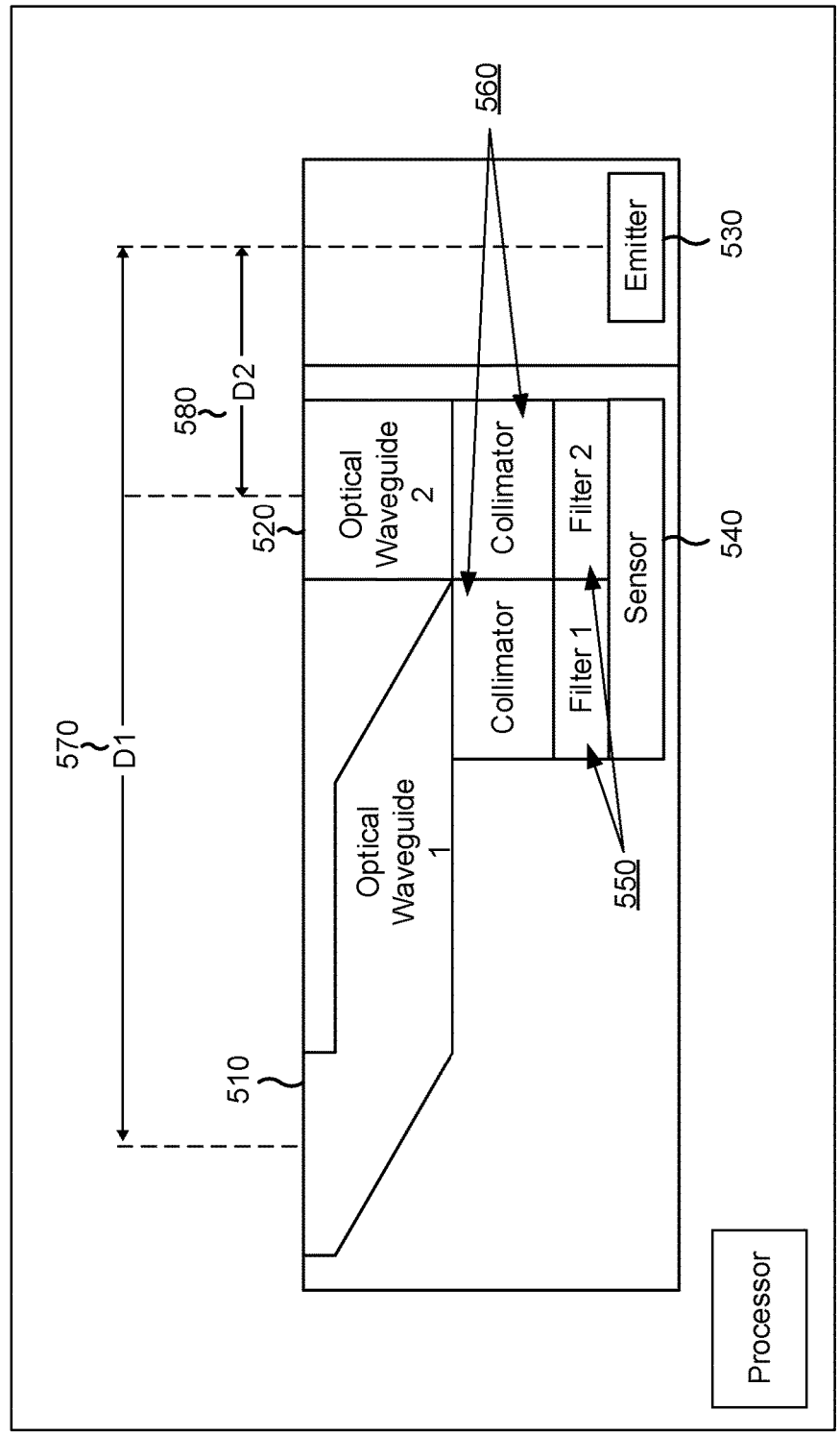

FIG. 5 shows an example implementation of a sensor device 500 including optical waveguides 510 and 520 that achieve multiple different sensor/emitter displacements. As shown, sensor device 500 includes optical waveguides 510 and 520, an emitter 530 (e.g., emitter 110/210/310/410), a sensor 540 (e.g., sensor 120/220/320/420), one or more filters 550 (e.g., filter 130/230/330/430), and one or more collimators 560.

Optical waveguide 510/520 includes a device capable of guiding light from one location to another location. For example, optical waveguide 510/520 may include an optical pickup, a light pipe, an optical fiber, and/or the like. Collimator 560 is a device capable of collimating light received via optical waveguide 510/520. For example, collimator 560 may include collimating optics and/or the like. An optical waveguide 510/520 may receive light generated by emitter 530 and may guide the light to collimator 560. For example, and as shown, optical waveguide 510 may guide light via a longer horizontal displacement than optical waveguide 520, meaning that displacement D1, shown by reference number 570, is larger than displacement D2, shown by reference number 580. Thus, sensor device 500 may achieve a variety of displacements using optical waveguides, which may allow for sensors and emitters to be provided in a smaller form factor. Furthermore, a plurality of displacements can be achieved using a single sensor that may be smaller than the sensor 320 described in connection with FIG. 3, which may reduce power consumption and simplify design. Furthermore, the filters 550 may be monolithic in design, which may simplify fabrication and implementation.

In some aspects, a characteristic of a filter or a sensor may be based on a displacement of the filter or sensor from an emitter. For example, a sensor associated with a larger displacement may be associated with a larger pixel size than a pixel size of a sensor associated with a smaller displacement, which may improve light collection to accommodate the dimmer signal, and enable larger displacements. As another example, a filter associated with a larger displacement may be associated with a wider filter channel to allow increased light collection, thereby accommodating dimmer signals and enabling larger displacements.

A sensor device (e.g., sensor device 100/200/300/400/500) may use a variety of techniques, or a combination of techniques, to differentiate the light transmitted by the emitters and/or the measurements determined using the light. For example, the sensor device may activate emitters at different times or in a particular pattern, and may determine measurements for emitters based on the times or the particular pattern. As another example, emitters may emit light at different wavelengths, and a filter may filter the different wavelengths so that wavelengths corresponding to different emitters are detected by different regions of the sensor or at different times.

Figure 6:
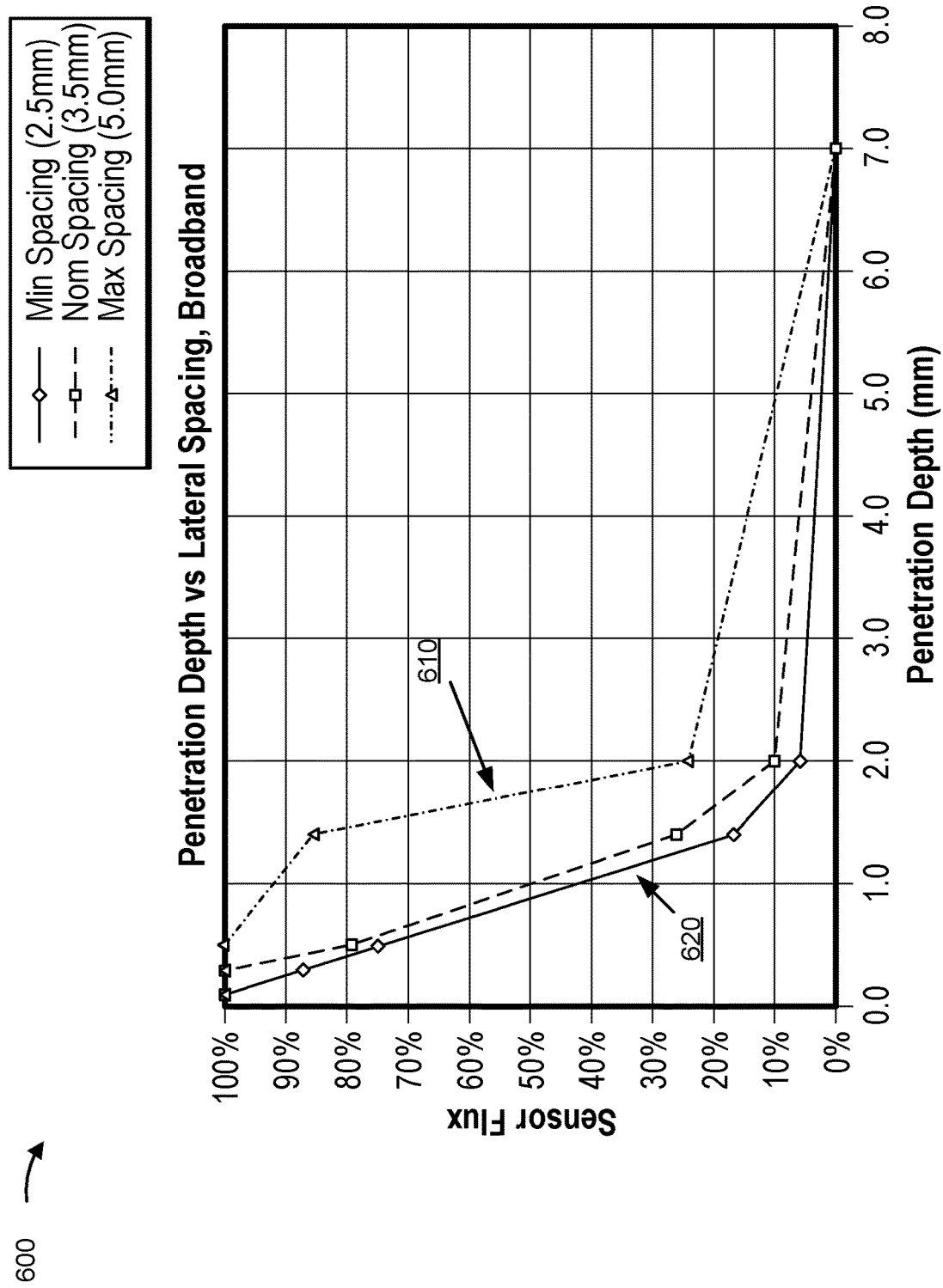
FIG. 6 is a diagram of an example relationship between measurement penetration depth and separation between a sensor and an emitter that relates to one or more example implementations described herein.

By providing multiple different displacements between sensors and emitters, different penetration depths for measurements on a measurement target may be achieved. For example, as shown by example 600 of FIG. 6, at a given penetration depth, a larger spacing (where spacing is used synonymously with displacement), such as a spacing of 5 mm between the sensor and the emitter as indicated by the line shown by reference number 610, may provide a higher sensor flux than a smaller spacing, such as a spacing of 2.5 mm shown by reference number 620. Thus, by combining smaller and larger displacements, improved performance at a given penetration depth may be achieved, while also enabling measurements at a shallower penetration depth, such as a measurement concurrent with the measurement at the given penetration depth.

As indicated above, FIGS. 1-6 are provided as one or more examples. Other examples may differ from what is described with regard to FIGS. 1-6. Furthermore, any one or more of the devices shown in FIGS. 1-6 may include one or more collimators or collimating optics similar to collimator 560 of FIG. 5.

Figure 7:
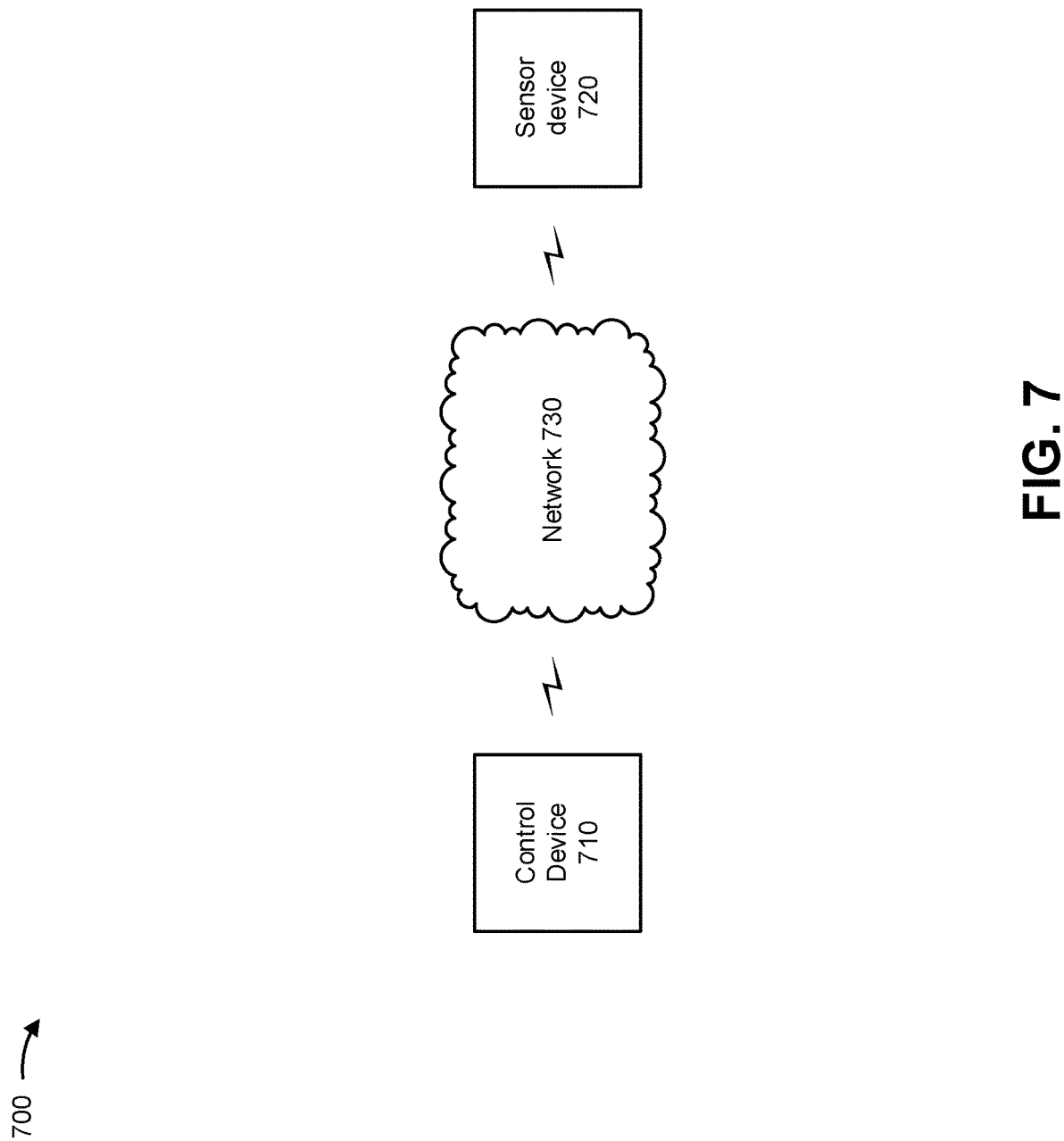
FIG. 7 is a diagram of an example environment in which systems and/or methods described herein may be implemented.

FIG. 7 is a diagram of an example environment 700 in which systems and/or methods described herein may be implemented. As shown in FIG. 7, environment 700 may include a control device 710, a sensor device 720, and a network 730. Devices of environment 700 may interconnect via wired connections, wireless connections, or a combination of wired and wireless connections.

Control device 710 includes one or more devices capable of storing, processing, and/or routing information associated with spectroscopic measurement. For example, control device 710 may include a server, a computer, a wearable device, a cloud computing device, and/or the like. In some implementations, control device 710 may be associated with a particular sensor device 720. In some implementations, control device 710 may be associated with multiple sensor devices 720. In some implementations, control device 710 may receive information from and/or transmit information to another device in environment 700, such as sensor device 720.

Sensor device 720 includes one or more devices capable of performing a spectroscopic measurement on a sample. For example, sensor device 720 may include a spectrometer device that performs spectroscopy (e.g., vibrational spectroscopy, such as a near infrared (NIR) spectrometer, a mid-infrared spectroscopy (mid-IR), Raman spectroscopy, and/or the like). In some implementations, sensor device 720 may be incorporated into a wearable device, such as a wearable spectrometer and/or the like. In some implementations, sensor device 720 may receive information from and/or transmit information to another device in environment 700, such as control device 710. In some implementations, sensor device 720 includes one or more of the components described in connection with sensor device 100/200/300/400/500.

Network 730 may include one or more wired and/or wireless networks. For example, network 730 may include a cellular network (e.g., a long-term evolution (LTE) network, a 3G network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, and/or the like, and/or a combination of these or other types of networks.

The number and arrangement of devices and networks shown in FIG. 7 are provided as an example. In practice, there may be additional devices and/or networks, fewer devices and/or networks, different devices and/or networks, or differently arranged devices and/or networks than those shown in FIG. 7. Furthermore, two or more devices shown in FIG. 7 may be implemented within a single device, or a single device shown in FIG. 7 may be implemented as multiple, distributed devices. For example, although control device 710 and sensor device 720 are described, herein, as being two separate devices, control device 710 and sensor device 720 may be implemented within a single device. Additionally, or alternatively, a set of devices (e.g., one or more devices) of environment 700 may perform one or more functions described as being performed by another set of devices of environment 700.

Figure 8:
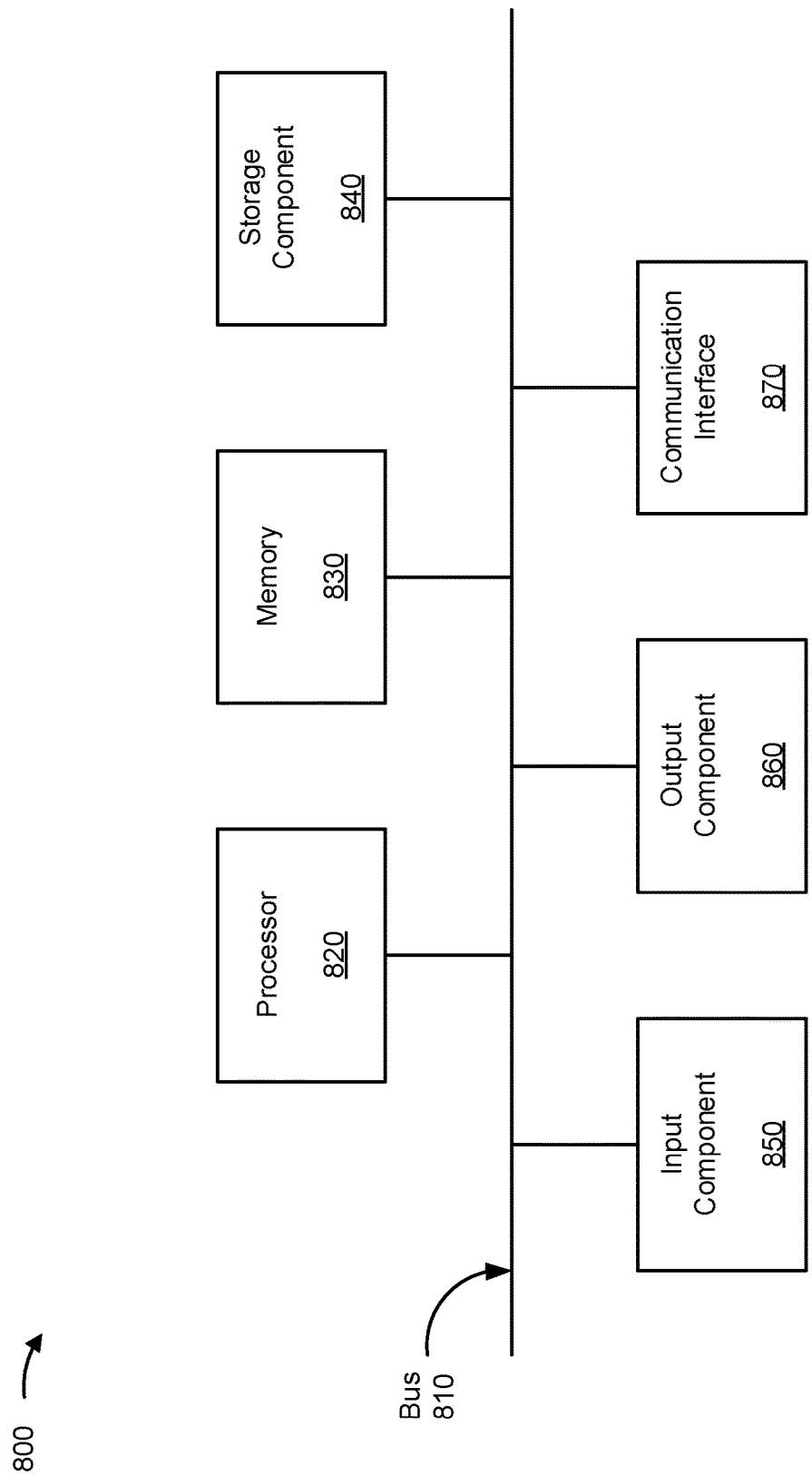
FIG. 8 is a diagram of example components of one or more devices of FIG. 7.

FIG. 8 is a diagram of example components of a device 800. Device 800 may correspond to control device 710 and sensor device 720. In some implementations, control device 710 and/or sensor device 720 may include one or more devices 800 and/or one or more components of device 800. As shown in FIG. 8, device 800 may include a bus 810, a processor 820, a memory 830, a storage component 840, an input component 850, an output component 860, and a communication interface 870.

Bus 810 includes a component that permits communication among multiple components of device 800. Processor 820 is implemented in hardware, firmware, and/or a combination of hardware and software. Processor 820 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 820 includes one or more processors capable of being programmed to perform a function. Memory 830 includes a random access memory (RAM), a read only memory (ROM), and/or another type of dynamic or static storage device (e.g., a flash memory, a magnetic memory, and/or an optical memory) that stores information and/or instructions for use by processor 820.

Storage component 840 stores information and/or software related to the operation and use of device 800. For example, storage component 840 may include a hard disk (e.g., a magnetic disk, an optical disk, and/or a magneto-optic disk), a solid state drive (SSD), a compact disc (CD), a digital versatile disc (DVD), a floppy disk, a cartridge, a magnetic tape, and/or another type of non-transitory computer-readable medium, along with a corresponding drive.

Input component 850 includes a component that permits device 800 to receive information, such as via user input (e.g., a touch screen display, a keyboard, a keypad, a mouse, a button, a switch, and/or a microphone). Additionally, or alternatively, input component 850 may include a component for determining location (e.g., a global positioning system (GPS) component) and/or a sensor (e.g., an accelerometer, a gyroscope, an actuator, another type of positional or environmental sensor, and/or the like). Output component 860 includes a component that provides output information from device 800 (via, e.g., a display, a speaker, a haptic feedback component, an audio or visual indicator, and/or the like).

Communication interface 870 includes a transceiver-like component (e.g., a transceiver, a separate receiver, a separate transmitter, and/or the like) that enables device 800 to communicate with other devices, such as via a wired connection, a wireless connection, or a combination of wired and wireless connections. Communication interface 870 may permit device 800 to receive information from another device and/or provide information to another device. For example, communication interface 870 may include an Ethernet interface, an optical interface, a coaxial interface, an infrared interface, a radio frequency (RF) interface, a universal serial bus (USB) interface, a wireless local area network interface, a cellular network interface, and/or the like.

Device 800 may perform one or more processes described herein. Device 800 may perform these processes based on processor 820 executing software instructions stored by a non-transitory computer-readable medium, such as memory 830 and/or storage component 840. As used herein, the term "computer-readable medium" refers to a non-transitory memory device. A memory device includes memory space within a single physical storage device or memory space spread across multiple physical storage devices.

Software instructions may be read into memory 830 and/or storage component 840 from another computer-readable medium or from another device via communication interface 870. When executed, software instructions stored in memory 830 and/or storage component 840 may cause processor 820 to perform one or more processes described herein. Additionally, or alternatively, hardware circuitry may be used in place of or in combination with software instructions to perform one or more processes described herein. Thus, implementations described herein are not limited to any specific combination of hardware circuitry and software.

The number and arrangement of components shown in FIG. 8 are provided as an example. In practice, device 800 may include additional components, fewer components, different components, or differently arranged components than those shown in FIG. 8. Additionally, or alternatively, a set of components (e.g., one or more components) of device 800 may perform one or more functions described as being performed by another set of components of device 800.

Figure 9:
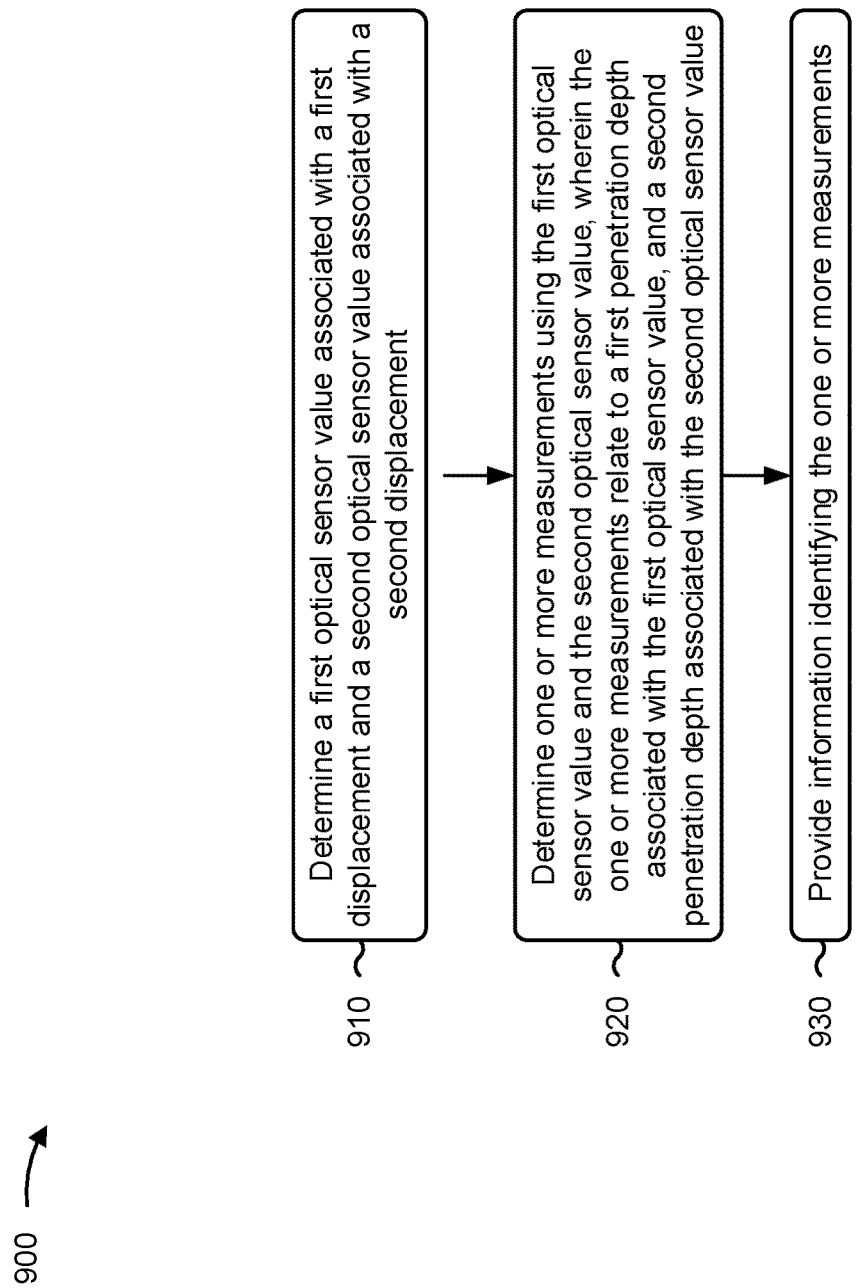
FIG. 9 is a flowchart of an example process for determining measurements at two or more different measurement depths based on two or more separations between sensors and emitters.

FIG. 9 is a flow chart of an example process 900 for determining measurements at two or more different measurement depths based on two or more separations between sensors and emitters. In some implementations, one or more process blocks of FIG. 9 may be performed by a sensor device (e.g., sensor device 100/200/300/400/500/720). In some implementations, one or more process blocks of FIG. 9 may be performed by another device or a group of devices separate from or including the sensor device, such as control device 710 and/or the like. In some aspects, the sensor device includes one or more optical sensors.

As shown in FIG. 9, process 900 may include determining a first optical sensor value associated with a first displacement and a second optical sensor value associated with a second displacement (block 910). For example, the sensor device (e.g., using processor 140/820, sensor 120/220/320/420/540, and/or the like) may determine a first optical sensor value associated with a first displacement and a second optical sensor value associated with a second displacement, as described above. In some implementations, the first displacement is between an emitter associated with the first optical sensor value and a sensing location used to determine the first optical sensor value, and the second displacement is between an emitter associated with the second optical sensor value and a sensing location used to determine the second optical sensor value. In some implementations, the first displacement is different from the second displacement.

As further shown in FIG. 9, process 900 may include determining one or more measurements using the first optical sensor value and the second optical sensor value, wherein the one or more measurements relate to a first penetration depth associated with the first optical sensor value, and a second penetration depth associated with the second optical sensor value (block 920). For example, the sensor device (e.g., using processor 140/820, memory 830, storage component 840, and/or the like) may determine one or more measurements using the first optical sensor value and the second optical sensor value, as described above. In some implementations, the one or more measurements relate to a first penetration depth associated with the first optical sensor value, and a second penetration depth associated with the second optical sensor value. For example, the one or more measurements may include respective spectrometry measurements, health-related measurements, and/or the like.

As further shown in FIG. 9, process 900 may include providing information identifying the one or more measurements (block 930). For example, the sensor device (e.g., using processor 140/820, memory 830, storage component 840, input component 850, output component 860, communication interface 870 and/or the like) may provide information identifying the one or more measurements, as described above. In some implementations, the sensor device may provide the information identifying the one or more measurements to a control device, for storage by the sensor device, via a user interface, and/or the like.

Process 900 may include additional implementations, such as any single implementation or any combination of implementations described below and/or in connection with one or more other processes described elsewhere herein.

In a first implementation, the emitter associated with the first optical sensor value and the emitter associated with the second optical sensor value are a same emitter.

In a second implementation, alone or in combination with the first implementation, the emitter associated with the first optical sensor value and the emitter associated with the second optical sensor value are different emitters.

In a third implementation, alone or in combination with one or more of the first and second implementations, the sensing location used to determine the first optical sensor value and the sensing location used to determine the second optical sensor value are a same sensing location.

In a fourth implementation, alone or in combination with one or more of the first through third implementations, the sensing location used to determine the first optical sensor value and the sensing location used to determine the second optical sensor value are different sensing locations.

In a fifth implementation, alone or in combination with one or more of the first through fourth implementations, the emitter associated with the first optical sensor value and the emitter associated with the second optical sensor value are a same emitter, and the first optical sensor value and the second optical sensor value are determined using a single optical sensor.

In a sixth implementation, alone or in combination with one or more of the first through fifth implementations, the first displacement is greater than the second displacement, and the first optical sensor value is determined using an integration time that is longer than an integration time used to determine the second optical sensor value.

In a seventh implementation, alone or in combination with one or more of the first through sixth implementations, the first displacement is greater than the second displacement, and the emitter associated with the first optical sensor value uses a greater transmission power than a transmission power used by the emitter associated with the second optical sensor value.

In an eighth implementation, alone or in combination with one or more of the first through seventh implementations, the one or more measurements comprise one or more spectroscopy measurements.

In a ninth implementation, alone or in combination with one or more of the first through eighth implementations, the sensor device includes a first optical waveguide connecting the sensing location used to determine the first optical sensor value and an optical sensor of the one or more optical sensors, and a second optical waveguide connecting the sensing location used to determine the second optical sensor value and the optical sensor.

In a tenth implementation, alone or in combination with one or more of the first through ninth implementations, the sensor device includes a first optical filter associated with an optical sensor of the one or more optical sensors, and a second optical filter associated with the optical sensor, wherein the first optical filter corresponds to the sensing location associated with the first optical sensor value and the second optical filter corresponds to the sensing location associated with the second optical sensor value.

In an eleventh implementation, alone or in combination with one or more of the first through tenth implementations, the first optical filter and the second optical filter cover different regions of the optical sensor.

In a twelfth implementation, alone or in combination with one or more of the first through eleventh implementations, the first optical filter is configured to filter light from the first optical waveguide and the second optical filter is configured to filter light from the second optical waveguide.

In a thirteenth implementation, alone or in combination with one or more of the first through twelfth implementations, the one or more optical sensors are a single optical sensor.

In a fourteenth implementation, alone or in combination with one or more of the first through thirteenth implementations, the one or more optical sensors comprise a single optical sensor, and the emitter used to determine the first optical sensor value and the emitter used to determine the second optical sensor value are different emitters.

In a fifteenth implementation, alone or in combination with one or more of the first through fourteenth implementations, the one or more optical sensors comprise a plurality of optical sensors, and the emitter used to determine the first optical sensor value and the emitter used to determine the second optical sensor value comprise a same emitter.

In a sixteenth implementation, alone or in combination with one or more of the first through fifteenth implementations, the one or more optical sensors comprise a plurality of optical sensors, and the emitter used to determine the first optical sensor value and the emitter used to determine the second optical sensor value are different emitters.

In a seventeenth implementation, alone or in combination with one or more of the first through sixteenth implementations, each optical sensor of the plurality of optical sensors is associated with a respective filter.

In an eighteenth implementation, alone or in combination with one or more of the first through seventeenth implementations, the sensor device includes one or more collimators used to collimate light for determining the first optical sensor value and the second optical sensor value.

Although FIG. 9 shows example blocks of process 900, in some implementations, process 900 may include additional blocks, fewer blocks, different blocks, or differently arranged blocks than those depicted in FIG. 9. Additionally, or alternatively, two or more of the blocks of process 900 may be performed in parallel.

The foregoing disclosure provides illustration and description, but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A sensor device, comprising:
a first optical waveguide to guide first light from a single emitter that includes a light emitting diode (LED),
wherein the first optical waveguide is located a first distance from the LED;
a second optical waveguide to guide second light from the LED,
wherein the second optical waveguide is located a second distance from the LED, and
wherein the second distance is different from the first distance;
a first collimator to collimate the first light received via the first optical waveguide;
a second collimator to collimate the second light received via the second optical waveguide;
a single sensor; and
one or more filters between the single sensor and one or more of the first collimator or the second collimator,
wherein the first collimator is between the first optical waveguide and the single sensor,
wherein the second collimator is between the second optical waveguide and the single sensor,
wherein the first collimator and the second collimator are on a first side of the single sensor,
wherein the LED is on a second side of the single sensor, and
wherein the second side of the single sensor is different from the first side of the single sensor.

2. The sensor device of claim 1, further comprising:
the single emitter,
wherein the single emitter is configured to generate the first light and the second light.

3. The sensor device of claim 1, wherein the first distance is longer than the second distance.

4. The sensor device of claim 1, wherein the first optical waveguide guides the first light via a longer horizontal displacement than the second optical waveguide guides the second light.

5. The sensor device of claim 1,
wherein the first optical waveguide is a first light pipe, and
wherein the second optical waveguide is a second light pipe.

6. The sensor device of claim 1, wherein the one or more filters comprise:
a first filter between the single sensor and the first collimator, and
a second filter between the single sensor and the second collimator.

7. A device, comprising:
a first optical waveguide to guide a first portion of light from a single emitter that is located a first distance from the first optical waveguide,
the single emitter including a light emitting diode (LED);
a second optical waveguide to guide a second portion of the light from the single emitter, the single emitter being located a second distance from the second optical waveguide, and the second distance being different from the first distance; and one or more collimators to collimate the light received via one or more of the first optical waveguide or the second optical waveguide, the first optical waveguide comprising a first dimension between where the first portion of the light is received by the first optical waveguide and where the first portion of the light is provided by the first optical waveguide, the second optical waveguide comprising a second dimension between where the second portion of the light is received by the second optical waveguide and where the second portion of the light is provided by the second optical waveguide, the second dimension being different from the first dimension, one or more of the first optical waveguide or the second optical waveguide being on a first side of the one or more collimators, the single emitter being on a second side of the one or more collimators, and the second side of the one or more collimators being different from the first side of the one or more collimators.

8. The device of claim 7, wherein the first optical waveguide includes an optical pickup, a light pipe, or an optical fiber.

9. The device of claim 7, wherein the second optical waveguide guides the second portion of the light via a longer horizontal displacement than the first optical waveguide.

10. The device of claim 7, further comprising:
a single sensor to receive the light after the first portion of the light and the second portion of the light after the light is collimated by the one or more collimators.

11. The device of claim 7, further comprising:
a single sensor,
wherein the one or more collimators are between the single sensor and a plurality of optical waveguides that include the first optical waveguide and the second optical waveguide.

12. A device, comprising:
a first optical waveguide to guide first light from a first location that is located a first distance from a single emitter that includes a light emitting diode (LED);
a second optical waveguide to guide second light from a second location that is located a second distance from the single emitter,
wherein the second distance is different from the first distance;

one or more collimators to receive one or more of the first light or the second light; and
a sensor to receive the first light from the first optical waveguide and the second light from the second optical waveguide,
wherein the first optical waveguide and the second optical waveguide are on a first side of the sensor,
wherein the single emitter is on a second side of the sensor, and
wherein the second side of the sensor is different from the first side of the sensor.

13. The device of claim 12, further comprising:
the single emitter,
wherein the single emitter is configured to generate the first light and the second light.

14. The device of claim 12, wherein the first distance is longer than the second distance.

15. The device of claim 12,
wherein the one or more collimators include:
a first collimator, and
a second collimator, and
wherein the device further comprises:
a first filter between the sensor and the first collimator; and
a second filter between the sensor and the second collimator.

16. The device of claim 15,
wherein the first collimator is between the first optical waveguide and the first filter, and
wherein the second collimator is between the second optical waveguide and the second filter.

17. The device of claim 12, wherein the one or more collimators include:
a first collimator to receive the first light from the first optical waveguide, collimate the first light, and provide the first light towards the sensor; and
a second collimator to receive the second light from the second optical waveguide, collimate the second light, and provide the second light towards the sensor.

18. The device of claim 12,
wherein the first optical waveguide is a first light pipe or a first optical pickup, and
wherein the second optical waveguide is a second light pipe or a second optical pickup.

19. The device of claim 12, further comprising:
a first filter between the sensor and the first optical waveguide; and
a second filter between the sensor and the second optical waveguide.

20. The device of claim 19, wherein the first filter and the second filter are monolithic in design.

* * * * *